US006309819B1

(12) United States Patent
Wakefield

(10) Patent No.: US 6,309,819 B1
(45) Date of Patent: *Oct. 30, 2001

(54) **DIAGNOSTIC AND THERAPEUTIC SYSTEM FOR CROHN'S DISEASE AND *COLITIA ULCEROSA***

(76) Inventor: Andrew Jeremy Wakefield, 43 Taylor Avenue Kew Gardens, Surrey TW9 4EB (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/913,982
(22) PCT Filed: Mar. 22, 1996
(86) PCT No.: PCT/GB96/00706
  § 371 Date: Nov. 10, 1997
  § 102(e) Date: Nov. 10, 1997
(87) PCT Pub. No.: WO96/30544
  PCT Pub. Date: Oct. 3, 1996

(30) Foreign Application Priority Data

Mar. 28, 1995 (GB) .................................... 9506298

(51) Int. Cl.⁷ .............................. C12Q 1/70; C12Q 1/68; C12P 19/34
(52) U.S. Cl. ................................ 435/5; 435/6; 435/91.2; 435/91.21
(58) Field of Search .......................... 435/6, 91.2, 91.21; 536/24.33, 24.31, 24.32

(56) References Cited

U.S. PATENT DOCUMENTS 4,871,759  10/1989  Mercer ................................. 514/398

OTHER PUBLICATIONS

BMJ, Jun. 5, 1998 316(7146) 1745–1746.*
Communicable Disease Report. CDR Weekly. (Mar. 27, 1998) 8(13): 113.*
Communicable Disease Report. CDR Weekly (Feb. 27, 1998) 8(9): 75, 78.*
Communicable Disease Report. CDR Weekly (Apr. 3, 1998) 8(14): 123, 126.*
Mori. Biologicals (1994), 22: 179–195.*
Commicable Disease Report–CDR Weekly (Jan. 30, 1998) 8(5): 41,45.*
BMJ (Jan. 17, 1998) 316 (125), p. 166.*
Afzal et al. J. Med. Virol. 55: 243–249 (1998).*
Bellini et al., "Virology of Measles Virus," *J. Infect. Dis.* 1994 170 (Suppl 1), 15–23.
Chirgwin et al., "Isolation of biologically active ribonucleic acid from sources enriched in ribonuclease," *Biochem.* 1979 18, 5294–5299.

Farrington et al, "Letters to the Editor," *Lancet* 1995 345, 1362–1364.

Fidler et al., "Specific detection of *mycobacterium paratruerculosis* DNA associated with granulomatous tissue in Chron's disease," *Gut* 1994 35, 506–510.

Gitnick et al., "Electron microscopic studies of viral agents in Crohn's disease," *Lancet* 1976 11, 217–219.

Haga et al., "Absence of measles viral genomic sequence in intestinal tissue from Crohn's disease by nested polymerase chain reaction," *Gut* 1996 38, 211–215.

Knibbs et al., "Ultrastructural Evidence of Paramyxovirus in two French families with Crohn's disease," *Gastro.* 1993 104, A726.

Koschel et al, "Measles Virus Antisense Sequences Specifically Cure Cells Persistently Infected with Measles Virus", *Virol.* 1995, 207 (1), 168–178.

Lewin et al., "Persistent measles virus infection of the intestine: confirmation by immunogold electron microscope," *Gut* 1995 36, 564–569.

Liu et al., "Immunocytochemical evidence of *listeria, escherichia coli* and *streptoccocus* antigens in Crohn's disease," *Gastro.* 1995 108, 1396–1404.

Sanderson et al., "*Mycobacterium paratruberculosis* DNA in Crohn's disease," *Gut* 1992 33, 890–898.

Smith et al., "Viral Association with Crohn's Disease," *Ann. Med.* 1993 25 (6), 557–561.

Wakefield A. J., "Evidence of Persistent Measles Virus Infection in Crohn's Disease," *J. Med. Virol.* 1993 39 (4), 345–353.

Wakefield A. J., "Measles Virus in Crohn's Disease [letter; comment]", *Lancet* 1995 345 8950), 660.

* cited by examiner

*Primary Examiner*—Lisa B. Arthur
(74) *Attorney, Agent, or Firm*—Licata & Tyrrell P.C.

(57) ABSTRACT

The present invention relates to a diagnostic system for the detection of Crohn's disease and ulcerative colitis by means of nucleotide amplification reactions, in situ or in vitro which detection means are specific for the measles virus and are capable of distinguishing between the "wild" type and the attenuated measles virus strains. The invention further provides a use in the manufacture of a medicament for the treatment of Crohn's disease and/or ulcerative colitis which medicament comprises a suitable vector carrying antisense RNA to specific viral proteins which are consequently inhibited from being expressed in the host.

17 Claims, 7 Drawing Sheets

Figure 3D:
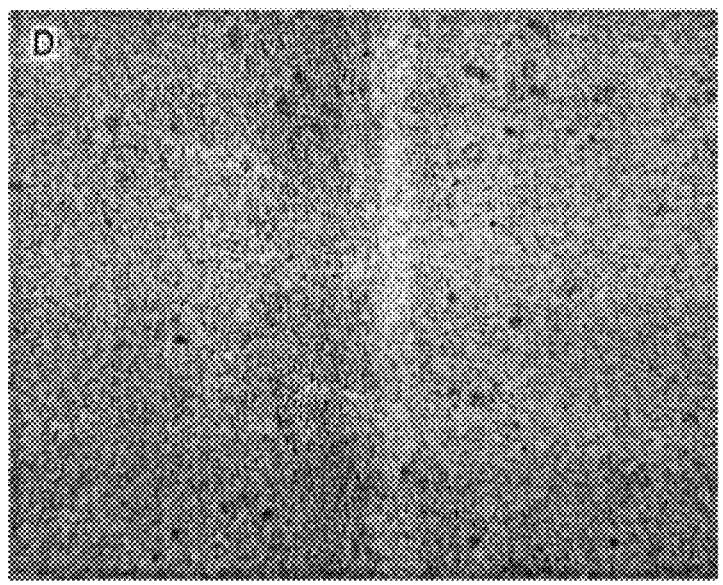
Figure 4A:
Figure 4B:

Fig.3a
Fig.3b
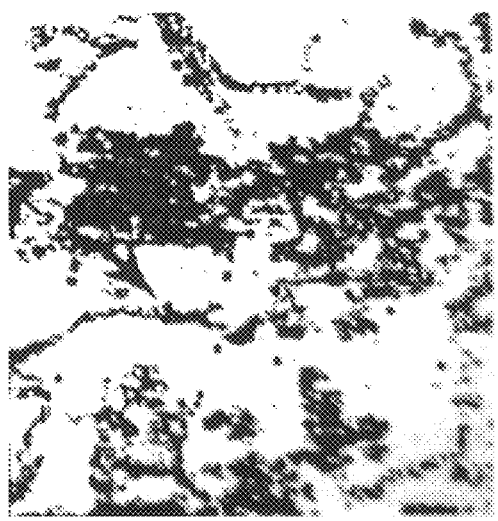
Fig.3c
Fig.3c

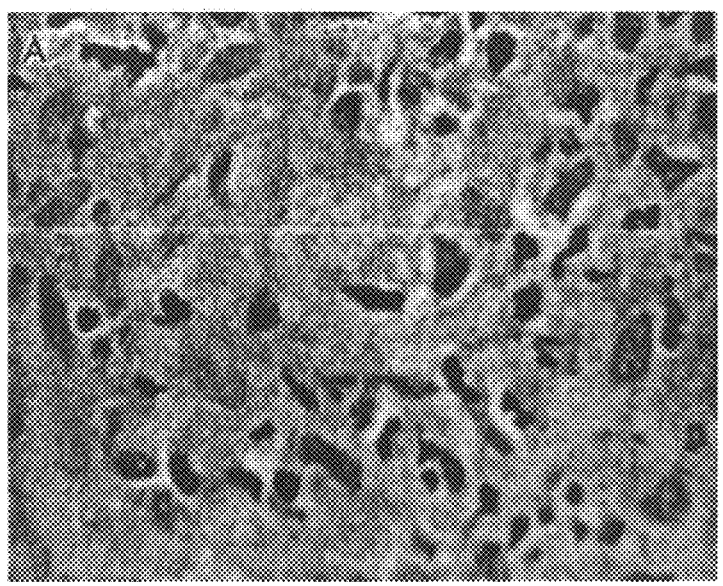
*Fig.5a*
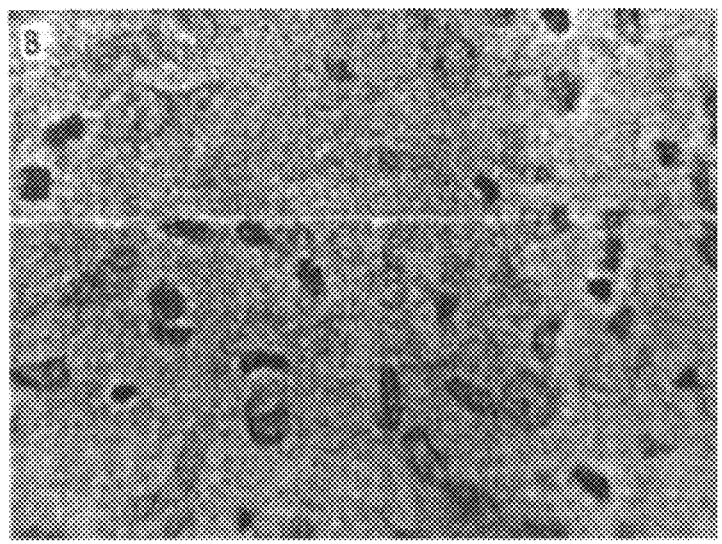
*Fig.5b*
*Fig.5c*
*Fig.5d*

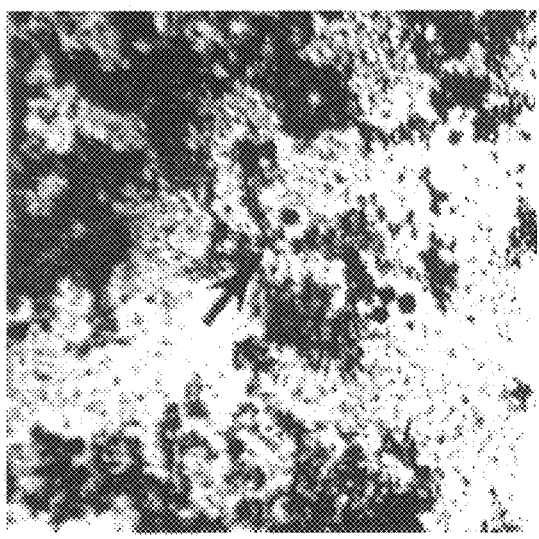
Fig.5d
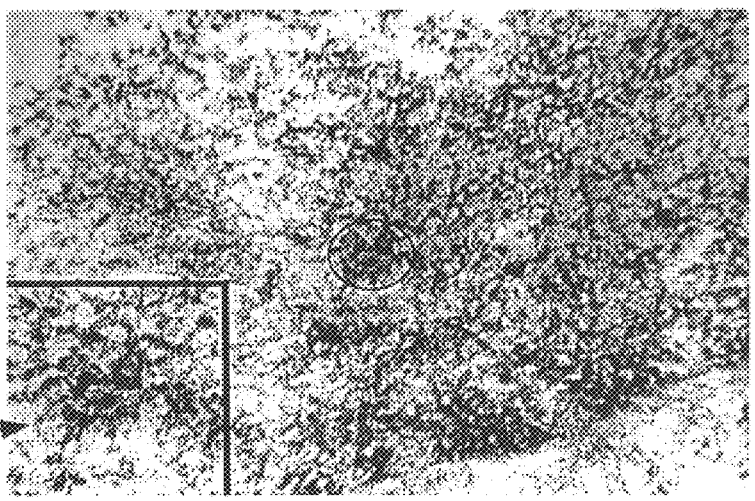
Fig.5e
Fig.5f
Fig.5f

DIAGNOSTIC AND THERAPEUTIC SYSTEM FOR CROHN'S DISEASE AND *COLITIA ULCEROSA*

This application has been filed under 35 U.S.C. 371 from PCT/GB96/00706 on Mar. 22, 1996.

The present invention relates to a diagnostic system for the detection of Crohn's Disease and ulcerative colitis and to a therapeutic system derived therefrom. No such diagnostic system is currently available.

Until recently there has been no definite cause attributable to the onset of Crohn's Disease or ulcerative colitis which have remained substantially incurable. The best that medicine can provide is some alleviation of the symptoms.

Crohn's Disease afflicts approximately 4 patients per 100,000 of the population, or in the United Kingdom 2,200 new cases per year. Because in its earlier stages Crohn's Disease tends to present as bowel irritation which is much more common, a reliable diagnostic system is required.

Similarly the incidence of ulcerative colitis is sufficient to warrant early diagnosis to enable early treatment.

In Ann. Med. 1993, Volume 25(6), pages 557 to 561, the inventor and a colleage review the evidence for an association between Crohn's Disease and viral infection by various techniques. The inventor and colleagues also discusses observations which suggest measles virus is capable of causing persistent infection of the intestine, and thus Crohn's Disease may be caused by a granulomatous vasculitis in response to the virus in J. Med. Virol. 1993, Volume 39(4), pages 345 to 353.

Virology 1995, Volume 207(1), pages 168–178 addresses measles virus anti-sense sequences in the treatment of cells persistently infected with measles virus.

The applicant has thus shown that the causative agent for Crohn's Disease is the measles virus and accordingly the present invention utilises this finding to provide a diagnostic system for the location of an attenuated vaccine measles virus in bowel tissue, bowel products or in suitable body fluids such as blood or lymph. Continuing studies increasingly support the finding that measles virus is the causative agent for ulcerative colitis. The invention also provides the basis for an anti-viral therapeutic system for the measles virus.

According therefore to a first aspect of the present invention, there is provided a diagnostic system for the detection of Crohn's Disease and ulcerative colitis which system comprises means for detecting attenuated vaccine measles virus RNA or a distinctive metabolic product thereof. Such means may be an antigenic system, or a system utilizing a nucleic acid amplification or hybridization reaction. In the latter case the invention specifically may provide means for performing a reverse transcription polymerase chain reaction or a nucleic acid sequence based amplification reaction or a ligase chain reaction. The systems may including a buffered primer specific for the reverse transcribed DNA from a RNA measles virus and/or an RNA template. The primer may comprise a 5' modified oligonucleotide sequence specific for any measles virus genomic or antigenomic or messenger RNA. The primer may be attached to a labelling or coagulating moiety such as a fluorochrome for ease of analysis.

The distinctive metabolic product may be selected from a gene sequence or metabolic product thereof to form a nucleocapsid protein, a phosphoprotein, a large protein, an RNA polymerase complex, a matrix protein, a fusion protein or a haemagglutinin protein, specific for the measles virus or a related paramyxovirus.

The nucleotide amplification may be a reverse transcription-polymerase chain reaction (RT-PCR) or nucleic acid sequence based amplification NASBA (or 3SR). In the former case a kit for performing the diagnostic tests as hereinbefore set forth may comprise:

(1) M-MLV reverse transcriptase;
(2) random hexamers and/or oligo $(Dt)_{12-18}$;
(3) a reaction buffer for (1) above;
(4) a PCR reaction buffer including Taq DNA polymerase
(5) a 5' modified PCR primer with reporter molecules.

Such a kit may further comprise a positive control which comprises measles virus RNA in solution at a known concentration and preferably a negative control or means for its provision.

We have however now found that NASBA is the preferred diagnostic method because it is significantly more sensitive for the detection of the measles virus.

According to a further aspect of the present invention there is provided a method for the in situ analysis of a tissue for Crohn's Disease or ulcerative colitis which method comprises the steps of:

a) obtaining a tissue sample and securing the same in an enclosed reaction container;
b) adding a reagent comprising a PCR buffer; $MgCL_2$, dNTP'S, random hexamers and diluting aqueously to a desired dilution factor;
c) subsequently closing the enclosed reaction container and adding M-MLV-RT and subjecting to heat cycling for at least one cycle;
d) treating with a washing buffer;
e) adding a buffered Taq DNA polymerase, $MgCL_2$, DNTP and a primer at a predetermined dilution in sterile distilled water and then heat cycling for at least 25 cycles; and
f) subsequently repeating step (d) and viewing for labelled product to indicate the presence of a wild or attenuated vaccine measles virus RNA.

In a further aspect of the present invention, there is provided a method for the in vitro analysis of a sample for Crohn's Disease or ulcerative colitis which method comprises the steps of extracting measles virus RNA from a tissue sample and a) adding thereto a buffer further comprising DTT, DNTP'S and R Nase inhibitor and oligo $(dT)_{12-18}$ and letting down to a desired aqueous concentration in an enclosed reaction container;
b) adding thereto M-MLV-RT and subjecting to incubation to provide a cDNA product;
c) purifying the product and adding thereto a PCR buffer along with $MgCL_2$, dNTP's and an outer primer;
d) subsequently adding Taq DNA polymerase and heating for at least 15 cycles;
e) recovering an aliquot of a so-formed reaction production and adding buffered PCR reaction mixture with inner primers and further Taq DNA polymerase and heat cycling for at least 15 cycles; and
f) moving the so-formed product and adding a loading dye and subjecting the resultant product to an electrophoresis to identify a resultant product band;
g) sequencing the amplified products, or hybridising the amplified products with a homologous or hetrologous specific probe to distinguish vaccine strain measles virus from "wild" type measles virus.

According to a further aspect of the present invention there is provided a medicament for the treatment of induced Crohn's Disease and/or ulcerative colitis which method prevents expression, replication, transcription, RNA processing and/or mRNA transport of the measles virus in the host. The medicament may include an attenuated vaccine measles virus antisense RNA for either genomic or antigenomic RNA and a vector. Alternatively, the medicament may comprise an attenuated vaccine measles virus peptide or carbohydrate antigen or a monoclonal or polyclonal antibody thereof. The invention also comprises a measles virus-specific nucleic acid based vaccine genome encoded into an expression system adapted to induce a specific immune response to the attenuated vaccine measles virus and/or its component antigens.

Using antisense RNA to the viral RNA including messenger RNA for the treatment of measles associated diseases alleviates the problem of side effects on host cellular functions. In the past such treatments have proved elusive partially due to the fact that it is extremely difficult to design inhibitors specific for the essential proteins of a virus. However, now in the prior art, the antisense RNA approach has been successfully used to inhibit viral genes of avian retrovirus, Rous sarcoma virus, human immunodificiency virus and simian immunodifeciency virus in cultured cells.

The invention provides a medication which comprises a suitable vector for uptake by the infected cells engineered to carry the appropriate measles virus antisense RNA designed to be targeted against the appropriate gene (e.g Nucleoprotein gene and/or Haemagglutonin gene) followed by a drug resistance gene (e.g Hygromycin B). The method of preparation of the medication is a modification of the methods in Koschel K. et al (1995), Virol. 207, 168–178.

The invention will now be described by way of illustration only in the following examples and with reference to the attached Figures wherein:

FIGS. 1A–1E shows Measles infected Vero cells immunostained with measles primary polyclonal antibody: areas of syncytial cytopathic effect exhibit intense cytoplasmic staining. Counterstained with Mayer's haematoxylin (original magnification ×350);

FIG. 1*b* shows Immunogold labelled measles infected Vero cells. Frequent foci of double and often larger clusters of gold particles are seen, associated with typical fibrillar arrays of nucleocapsids, 15–20 nm in diameter. Counterstained with uranyl acetate and Reynold's lead citrate (original magnification ×91,000);

FIG. 1*c* shows Measles infected Vero cells treated identically to 1*a*, but omitting the measles antibody primary (original magnification ×375);

FIG. 1*d* shows Measles infected Vero cells developed without measles primary antibody, but exposed to gold-conjugated secondary antibody; no labelling is seen (original magnification ×91,000);

FIG. 1*e* shows Mumps primary antibody on measles infected Vero cells, showing no signal (immunoperoxidase; original magnification ×400).

FIGS. 2A–2D shows Mumps infected Vero cells immunostained with mumps primary antibody showing cytoplasmic staining in infected cells (original magnification ×400);

FIG. 2*b* shows Mumps infected Vero cells treated identically to 2*a*, but omitting the mumps primary antibody (immunoperoxidase; original magnification ×400);

FIGS. 2*c* and 2*d* show Measles primary antibody on mumps infected Vero cells examined by immunoperoxidase (2*c*) (original magnification ×400) and immunogold (2*d*) (original magnification ×82,400). No antibody cross reactivity is seen. In 2*d*, the fine fibrillary arrays of mumps nucleocapsids are seen clearly;

FIGS. 3A–3D shows

SSPE: immunostaining for measles virus nucleocapsid protein in SSPE brain examined by light microscopy (FIG. 3*a*) original magnification ×400) and electron microscopy (FIGS. 3*b* and 3*c*). Intranuclear nucleocapsids are seen in FIG. 3*b*, frequently showing paired gold particles spanning individual nucleocapsids, demonstrated clearly in FIG. 3*c*, showing cytoplasmic signal (original magnifications; 3*b*×62,500, 3*c*×95,000). FIG. 3*c*, showing cytoplasmic signal (original agnifications; 3*b*×62,500, 3*c*×95,000). No signal is seen in identically processed tissue sections, in which the primary measles antibody was omitted (FIG. 3*d*; immunoperoxidase original magnification ×400);

FIGS. 4A–4B shows

Measles appendicitis: immunoperoxidase treated sections stained for measles virus N protein. Positive signal is seen in an endothelial cell syncytium (FIG. 4*a*) (erythrocytes arrowed) (original magnification ×100) and a Warthin Finkeldey giant cell (FIG. 4*b*) (original magnification ×800);

FIGS. 5A–5E shows

Crohn's Disease: positive nuclear staining in macrophage-like cells in a focus of granulomatous inflammation (FIG. 5*a*; immunoperoxidase; original magnification ×600). Signal is not seen in an identically processed serial section, omitting the primary antibody (FIG. 5*b*, original magnification ×600). Positive immunogold labelling is seen in an identical cellular location and shows the characteristic paired signal (arrowed) FIG. 5*c*, original magnification ×71,000);

FIG. 5*d* (inset) shows a high power view of gold label distributed along the length of what appears to be a single nucleocapsid (original magnification ×139,000);

FIG. 5*e* shows nuclear staining in a macrophage in a focus of granulomatous inflammation from another case of Crohn's Disease. The paired signal is observed, particularly in the central cluster, shown magnified in 5*f*; this demonstrates clearly, the parallel arrays (arrowed) of a 17 nm diameter nucleocapsid spanned by the gold label (original magnifications; FIG. 5*e*×91,000, FIG. 5*f*×95,000). Staining was not observed in otherwise identically processed sections of Crohn's Disease when the measles primary antibody was omitted (FIG. 5*f*, original magnification ×54,000).

EXAMPLE 1

A study was conducted to confirm the viral origins of the nucleocapsid-like particles observed in bioassays of bowel tissue in Crohn's Disease or probably ulcerative colitis by co-localising these particles with a gold-labelled antibody specific for measles virus nucleocapsid protein. These particles have not previously been detected ultrastructurally in normal intestine.

Cell Culture

Vero (green monkey kidney) cells were cultured in 75 mm flasks using standard techniques. Confluent monolayers were infected with either Edmonston strain measles virus at a titre of $10^7$ plaque forming units per ml, or mumps virus (Taylor strain: PHLS Colindale, UK) at a $TCID_{50}$ (Tissue Culture Infectious Dose) of $10^4$; uninfected cells were used as a negative control. When >80% of cells showed cytopathic effect, monolayers were fixed using 1% glutaraldehyde/1% paraformaldehyde in phosphate buffered saline (PBS) for 30 minutes. The cells were scraped from the flask using platinum wire loop and the suspended cells were pelleted in Eppendorf tubes using a Beckman microfuge (Palo Alto, Calif., USA). Cell pellets were washed after fixation with PBS and dehydrated using dimethylformamide, 50, 70 and 90%×2 changes each of 10–20 minutes duration depending on the size of the block. The blocks were then infiltrated with a 50:50 mixture of dimethylformamide and LR White resin with 0.5% benzoin photoinitiator (TAAB Laboratories Equipment Ltd, Reading, UK) added, for 30–60 minutes followed by 100% resin for 1–2 hours. The blocks were embedded in closable embedding capsules using fresh LR White with photoinitiator. Polymerisation was carried out at 40° using a UV light source at 10 cm distance. The resin polymerised in 1–2 hours and the small amount of resin remaining unpolymerised under the closure was removed sing a cotton swab.

Tissue Reprocessed from Paraffin Blocks

Initially, archival formalin-fixed paraffin processed tissues with established measles infection were selected; these included cerebral tissue from a case of subacute sclerosing pan-encephalitis (SSPE), and appendix from a case of acute measles virus appendicitis (Gift of Dr H Reid, Chase Farm Hospital, Enfield). Six cases of granulomatous Crohn's Disease were selected that included 4 rectal biopsies and two appendices taken at the time of initial presentation (that is, before specific or immunosuppressive therapy was instituted). In both the positive controls and Crohn's Disease tissues, the diagnoses were established by standard clinical and histopathological criteria. Two cases of ileocecal tuberculosis (TB) were studied as granulomatous controls. Sections were cut from tissue blocks and immunostained with a polyclonal antibody specific for the measles virus nucleocapsid (N) protein (gift of J Stephenson and T Fookes, CAMR, Porton Down, UK) using an immunoperoxidase technique, as described previously (Wakefield AJ. J Med Virol 1993; 39;345–353). Serial tissue sections were processed with either omission of the primary antibody or exposure to mumps (a related paramyxovirus) specific monoclonal antibody (Seralab, Crawley, Sussex, UK) as negative controls. Cross-reactivity of the measles and mumps specific antibodies was examined in Vero cells infected with these viruses, prior to immunogold studies.

Processing for Electron Microscopy

Suitable areas of tissue were selected for immunogold analysis; these included areas that gave positive measles staining by immunoperoxidase, and foci of granulomatous inflammation in the cases of Crohn's Disease and ileocecal TB. Wedges of tissue were removed from the paraffin block using a single edged razor blade. The pieces were dewaxed with chloroform followed by rinsing in absolute alcohol. The tissue was then infiltrated with resin and embedded as described above.

Paraffin sections only were available on the acute measles appendicitis. A novel method was used to lift the tissue from the slide; the section was dewaxed and taken to absolute alcohol, it was then flooded with 50:50 mixture of alcohol and LR White resin with photoinitiator added for a further 15 minutes; it was then drained and the slide blotted to remove surplus resin. Drops of fresh resin were placed over the tissue and covered with plastic coverslips (Agar Scientific, Stansted, UK). The resin was then polymerised with UV at 4° C. for one hour. The coverslip was peeled off and unpolymerised resin removed. The resin containing the tissue was lifted by immersing the slide in liquid nitrogen for a few seconds. The pieces were then trimmed and mounted onto blank resin blocks using Permabond quick setting epoxy resin (Permabond Adhesives Ltd, Eastleigh, UK) Ultrathin sections were cut at 50–80 nm and immunostained as above.

Immunolabelling

Ultrathin section were cut at 70–80 nm and picked up onto Piliform (Agar Scientific, Stansted, UK) coated 300 mesh nickel grids (Gilder, Grantham, UK). The grids were incubated on drops of 5% normal goat serum in 0.1% BSA/PBS buffer for 30 minutes, they were then transferred to drops of primary—measles polyclonal antibody 1/100 in 0.1% BSA/PBS for 1 hour. Primary antibody was removed by washing on drops of PBS 5×5 minutes, the first transfer being made without removing any surplus liquid from the grid. Surplus buffer was removed on the remaining four changes by touching the edge on a piece of blotting paper, taking care not to allow the grid to dry out. The grids were then transferred to drops of gold conjugate (Biocell, Cardiff, UK) diluted 1/100 with PBS for 1 hour followed by washing with drops of PBS 2×5 minutes to remove unbound gold conjugate and a final rinse in distilled water. Sections were stained lightly with uranyl acetate and Reynold's lead citrate and viewed using a Philips 201 transmission electron microscope. Sections processed omitting the primary antibody, were included with all tissues as negative controls.

Measles-infected Vero Cells

Figure 1A:
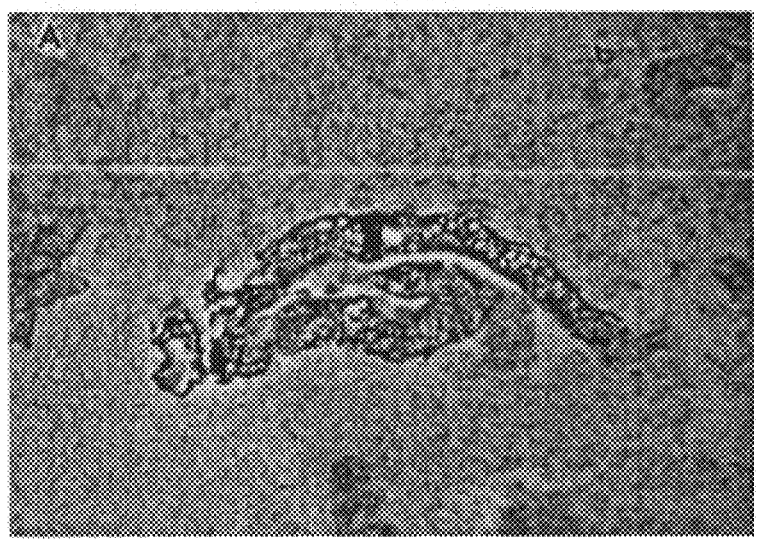
Figure 1B:
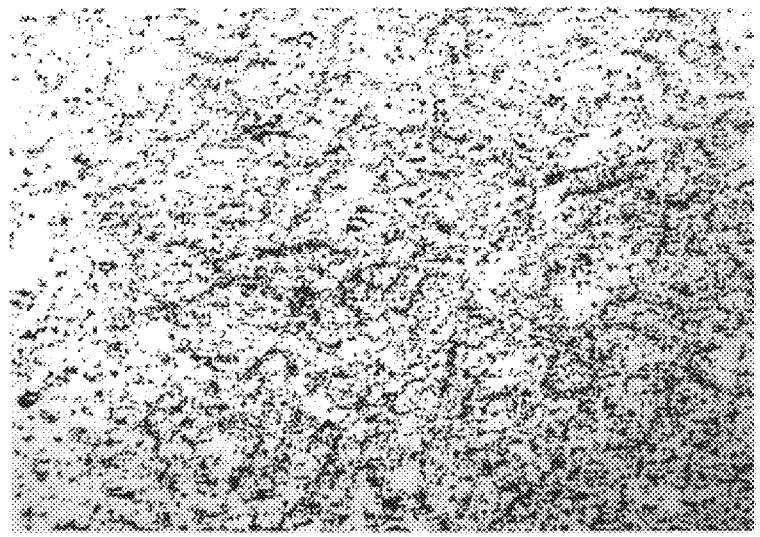
Figure 1C:
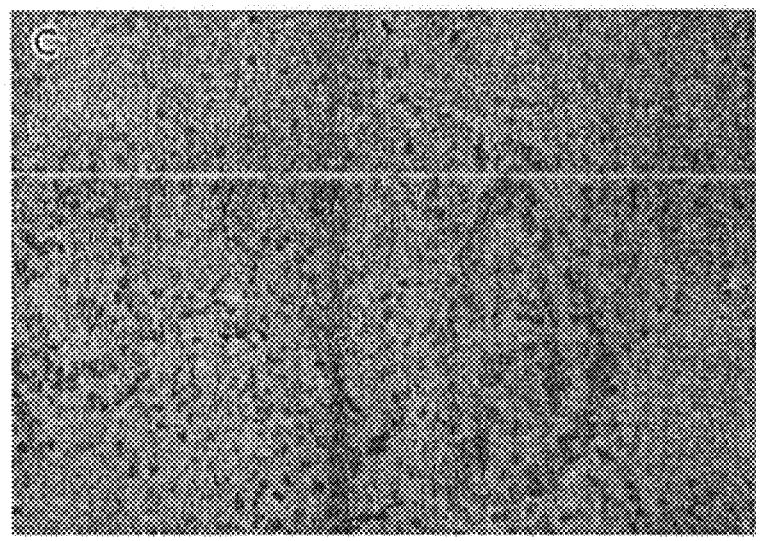
Figure 1D:
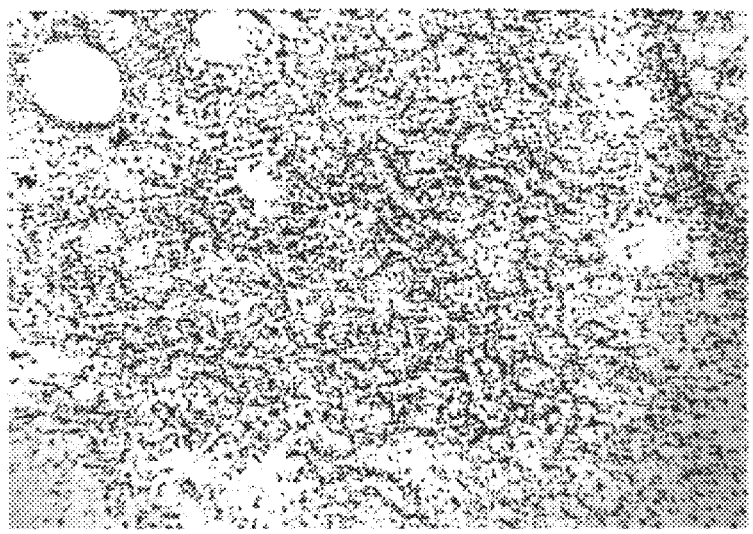
Figure 1E:
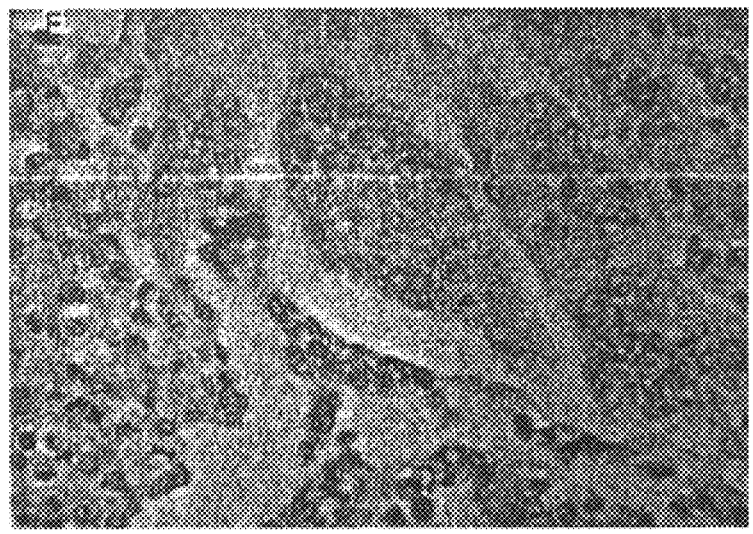

Vero cells that had been experimentally infected with measles virus exhibited positive immunoperoxidase and immunogold labelling (FIGS. 1a and 1b) that was not seen either in identically processed measles infected cells not exposed to the primary measles antibody (FIGS. 1c and 1d), or in measles infected cells exposed to the mumps primary antibody (FIG. 1e). Ultrastructurally, viral nucleocapsids consisted of characteristic parallel fibrillar structures of between 15 and 20 nm diameter.

Figure 2A:
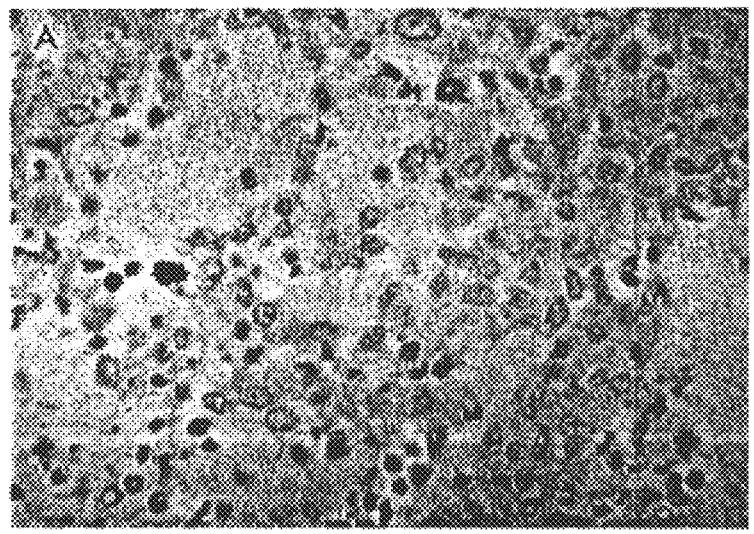
Figure 2B:
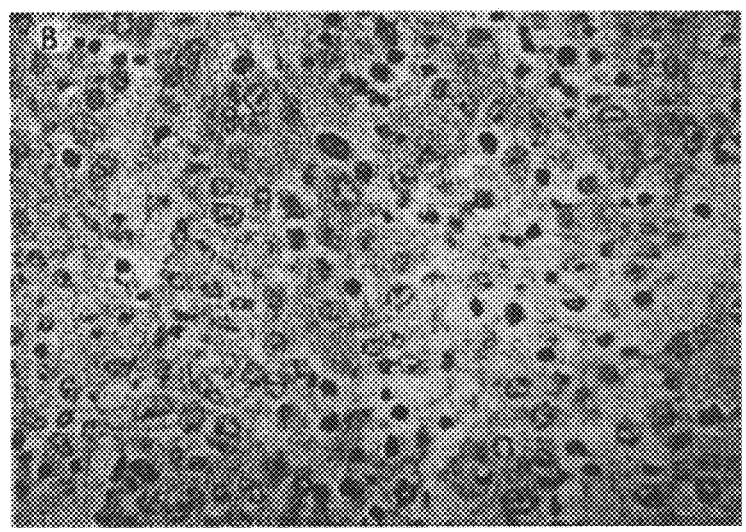
Figure 2C:
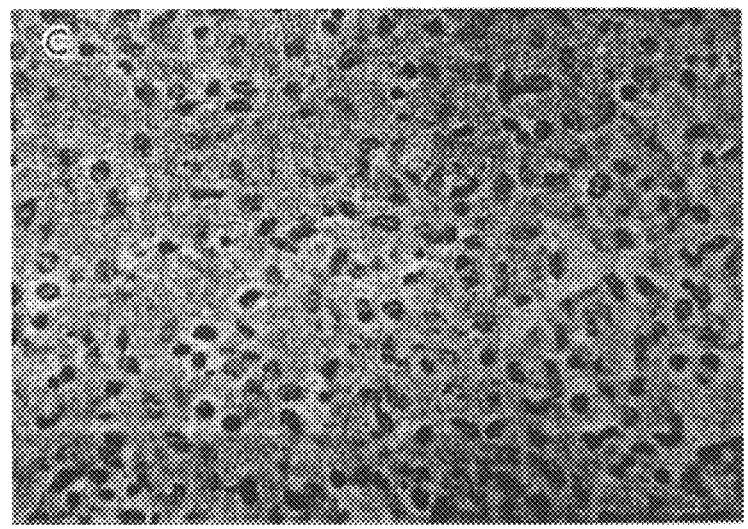
Figure 2D:
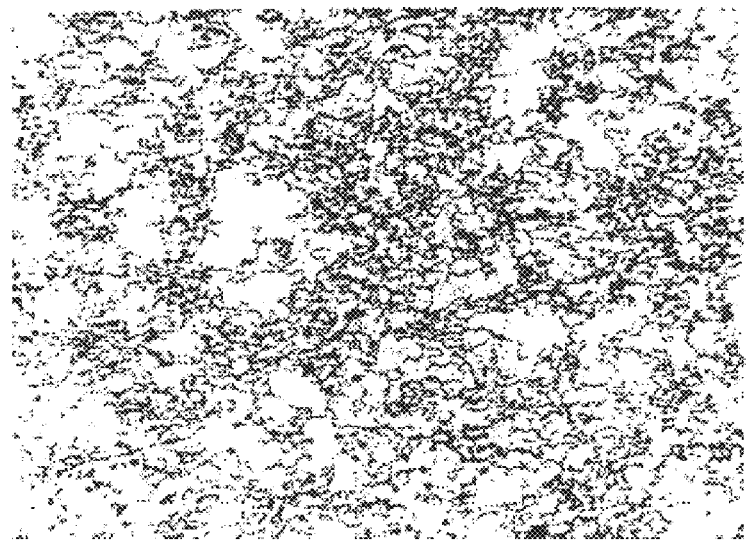

A characteristic pattern of labelling was observed in both nucleus and cytoplasm of infected cells that consisted of gold particles—grouped, often in pairs, and bound at discrete points along the viral nucleocapsids (FIG. 1b); this pattern was seen consistently in both infected cells and infected tissues, and was not seen in the very occasional background signal observed in control sections. Mumps infected Vero cells stained strongly by immunoperoxidase using the primary mumps antibody (FIG. 2a), but did not stain when the mumps primary antibody was omitted in otherwise identically processed cells. No signal was observed when the measles antibody was put onto mumps infected cells at either the light microscopic or ultrastructural levels.

Subacute Sclerosing Panencephalitis

Strong signal for measles virus as observed predominantly in the nuclei of infected cells, using both the immunoperoxidase technique on histological sections, and immunogold labelling of ultrathin sections of infected brain. Ultrastructurally, viral nucleocapsids were well preserved despite suboptimal fixation and paraffin processing. Again, the double immunogold signal on nucleocapsids was a consistent feature. No signal was observed on sections in which the primary measles antibody had been omitted, either at the light microscopic (FIG. 3d) or ultrastructural levels (data not shown).

Intestinal Tissues

The techniques were applied subsequently to measles-infected intestinal tissue—acute infected measles appendicitis—with similar results. Measles virus antigen was identified by the immunoperoxidase technique in endothelial cells, and macrophage-like cells including Warthin-Finkeldy giant cells, a classical feature of acute measles virus infection, and occasional lymphocytes within lymphoid follicles. Staining was not seen in negative control sections. Immunogold labelling confirmed the presence of the virus in the same cellular foci despite suboptimal preservation. No signal was observed in the absence of the primary antibody.

Of the six cases of Crohn's Disease examined, all were positive for measles by immunoperoxidase within cells consistent in morphology and location with histiocytic macrophages, endothelial cells and occasional lymphocytes; signal was not seen in sections that were either not exposed to the measles primary antibody, or exposed to mumps primary antibody. Five cases were positive by immunogold in the same cellular location, and viral particles exhibited the characteristic features of size, shape and immunogold labelling described above; in one case, signal was detected additionally, in a single crypt epithelial cell. In the fifth case, that was negative by immunogold, the focus of granulomatous inflammation present in the histological sections had "cut out" and could not be identified in the ultrathin section. Crohn's sections, processed in an identical manner, but excluding the measles primary antibody, were negative. Of the two cases of ileocecal TB that were examined, neither was positive by immunoperoxidase, although one case exhibited a low level of nuclear signal in a acrophage-like cell, by immunogold labelling.

This presents the first direct evidence of measles virus persistence in the intestine; that is, the co-localisation of a specific antibody with viral nucleocapsids at the ultrastructural level. The cellular localisation of measles virus in Crohn's tissues is consistent with that observed previously using different techniques (Wakefield AJ J Med Virol 1993; 39; 345–353; Knibbs DR, Gastroenterology, 1993; 104; A726 (Abstract)), and in different laboratories (Knibbs DR. Gastroenterology, 1993;104;A726 (Abstract)). The co-localisation of a specific antibody with particles that are, in terms of both size and morphology, identical to the target virus, is strong evidence for the presence of that virus; the characteristic pattern of labelling of nucleocapsids with gold particles provided a further, if unexpected degree of specificity. The detection of measles in one of two cases of ileocecal TB raises the possibility that persistently infected immune cells aggregate in foci of inflammation, and are unrelated to the primary cause of the granuloma. This notwithstanding, in Crohn's Disease tissues, the detection of measles virus within resident intestinal cells, including endothelium and epithelium, does suggest persistent intestinal infection. It is possible however that circulating immune cells within the same host may also be persistently infected.

Corticosteroids, a mainstay in the treatment of patients with Crohn's Disease, may predispose to permissive viral replication, and confound the question of persistence within the inflamed intestine; none of the patients whose tissues were examined in this study had received either corticosteroids or other immunosuppressive therapy.

EXAMPLE 2

The implied aetiological association of measles virus with Crohn's Disease is supported by detection of an immune response to infected cells in affected tissues. This example sought to detect and characterise in situ immune responses to measles virus in both acutely and persistently infected tissues, and in particular, Crohn's granulomata. Serial tissue sections from cases of Crohn's Disease (n=17), tuberculosis (n=9), acute intestinal ischaemia (n=5), acute measles pneumonitis (n=2), acute measles appendicitis (n=1), subacute sclerosing panencephalitis (SSPE; n=1), and measles inclusion body encephalitis (MIBE; n=1), were examined. Single and double immunohistochemical labelling was performed to identify both cytotoxic lymphocytes (CD8, TIA, perforin, Leu 7, CD45RO, CD45RA) and macrophages (KP1). The relationship of these cells to measles infected cells was identified by double immunolabelling with anti-measles virus nucleoprotein antibody. In both acute measles appendicitis and SSPE, $CD8^+/TIA^+$ cytotoxic lymphocytes (CTL) targeted infected cells. In the other tissues that were positive for measles virus including Crohn's Disease (13/17)—where staining was largely confined to granulomata, MIBE, fatal pneumonitis, and 1 tuberculous granuloma, infected cells appeared to be targeted by macrophages rather CTL. The CTL in Crohn's granulomata were Leu 7~ and perforin~/CD45RO~(naive). CTL in both tuberculous and Crohn's granulomata were similar in their peripheral distribution, number and phenotype. The data suggest that measles-specific CTL responses may be attenuated in Crohn's Disease compared with acute measles appendicitis and SSPE, and secondly, that an abnormal macrophage response to persistent measles virus infection of the intestine could result in granulomatous inflammation.

EXAMPLE 3

In an international collaborative study, serum measles IgM immunoreactivity was assayed by ELISA in consecutive outpatients with Crohn's Disease (n=95), ulcerative colitis (n=79), viral hepatitis (n=63) and blood donors (n=30). Results were compared with those obtained from a different commercial measles IgM assay, serum rubella and Epstein-Barr virus-specific IgM immunoreactivity, total serum IgM, Rheumatoid Factor and measles-specific IgG. Twenty patients with inflammatory bowel disease were studied serially over a four month period. At the ELISA cut-off point for confirmation of recent acute measles virus infection, there were no significant differences between groups. However, increased serum measles IgM immunoreactivity ($\geq$mean±2SD of blood donors) was significantly greater in patients with Crohn's Disease 39/95 (41%) and ulcerative colitis 33/79 (42%) compared with hepatitis patients 5/64 (8%) and normal controls 0/30 (0%) (p<0.001). Those positive by ELISA were also positive by indirect immunofluorescence on the same serum sample. Serum measles IgM immunoreactivity did not correlate with either total IgM, rubella or Epstein-Barr virus IgM (not raised), measles IgG, or disease activity. Patients not receiving steroids were more likely to have raised measles IgM immuunoreactivity (p<0.05). All sera examined for Rheumatoid Factor were negative. Of twenty patients with inflammatory bowel disease studied over four months, 55% showed raised measles IgM immunoreactivity at some stage during the follow-up. The data suggested an immunological response to measles virus in patients with Crohn's Disease and ulcerative colitis, supporting a potential aetiological role for this agent in inflammatory bowel disease.

EXAMPLE 4

The epidemiological association between Crohn's Disease and early measles virus exposure has been indicated either indirectly, on in studies of case-control design. In order to determine absolute risk estimates for in utero measles exposure and Crohn's Disease, maternity charts for all 25,000 deliveries at University Hospital, Uppsala, between 1940–1949 were reviewed; four cases of overt measles infection in the mother during pregnancy were identified. Offspring, and in two cases their mothers also, were interviewed, and case records reviewed. Cases, 1, 2 and 3 had undergone multiple intestinal resections; tissues, available from two cases, were examined by both routine histology, and immunohistochemistry and immunogold electronmicroscopy for measles. virus, using appropriate positive (brain; subacute sclerosing panencephalitis) and negative (no primary antibody, mumps infected cells) controls (Gut. 1995; 36: 564–9). Three cases of Crohn's Disease occurred in the four offspring; in each case the disease was preceded by recurrent, antibiotic resistant pneumonia. All had extensive ileal and colonic disease, two patients requiring intravenous feeding. Of the four cases, the only one to have suffered clinical acute measles disease, did not develop Crohn's Disease. Tissues from two cases of Crohn's Disease that were examined for measles virus antigen, were positive in foci of granulomatous and lymphocytic inflammation. The data indicate that in utero exposure to measles virus is a major risk factor for severe, extensive Crohn's Disease. Exposure at this time may lead to persistent infection, or alternatively, modify the response to the infection in later life, leading to virus persistence.

EXAMPLE 5

Immunogold electron microscopy was used to test for the presence of measles virus in intestinal tissue from patients with Crohn's Disease, and inflammatory and non-inflammatory disease controls. Formalin-fixed, paraffin-embedded tissue was reprocessed and stained with anti-measles nucleoprotein primary antibody followed by 10 nm gold-conjugated secondary antibody. Similarly processed brain tissue, taken from a patient with subacute sclerosing panencephalitis (SSPE), was used as the positive control. Duplicate sections of all tissues were processed without the primary antibody. In Crohn's Disease 8/9 foci of granulomatous inflammation and 0/4 foci of non-specific inflammation were positive for measles virus. Of control,s 0/5 ulcerative colitis tissues and 1/1 SSPE tissues were positive. Gold grain counts per nuclear field in both Crohn's granulomata and SSPE were highly significantly greater than controls, including non-granulomatous areas of Crohn's Disease ($p<0.0006$); in both diseases staining was confined to a small population of cells exhibiting characteristic cytopathology. These data support a role for measles virus in the aetiology of Crohn's Disease.

EXAMPLE 6

Kits for Measles Virus Detection

Measles is an RNA virus. The nucleic acid amplification mediated detection whether in situ or in vitro of this example is based on either reverse transcription—polymerase chain reaction (RT-PCR) or nucleic acid sequence based amplification NASBA (3SR).

The main components of the RT-PCR kit for measles detection in vi tro or in situ possess (i) Reverse transcriptase eg M-MLV reverse transcriptase (ii) Primers for first strand cDNA synthesis iii) reaction buffer for RT, (iv) PCR reaction buffer, (v) PCR primers which may be 5' modified with reporter molecules, eg fluorochromes.

Additionally an Amicon Microcon 30 size exclusion cartridge is optionally required for purification of the product from first strand DNA synthesis for in vitro amplifications.

Both kits preferably include a positive control, for example measles virus RNA, supplied as a solution at known concentration with which individuals using the kit can calibrate their results.

Additionally a negative control is required. This is preferably achieved by treatment of one portion of the sample to be tested with RNase A for 10 minutes at 37° C. prior to analysis. This is effective for both in situ and in vitro applications and additionally indicates any non-specific product formation from any DNA that may be present as a contaminant in the samples. It is therefore desirable to include Rnase A as an additional component in the kit.

Two basic protocols follow for a) in situ; and b) in vitro amplification.

EXAMPLE 7 a) Measles virus detection in situ—Kit 1

1) To the tissue section as prepared in Example 6 is added 75 $\mu$l of reagent (1). The slide is sealed in an enclosed reaction chamber such as that shown in PCT/GB95/00215 and placed on a flat block of a pHC3 Techne thermal cycler. With the enclosed reaction container so positioned 200 units of M-MLV RT are added and heated for 2 hours at 42° C., followed by five minutes at 95° C., followed by five minutes at 15° C. to complete a first heating cycle.

2) The slide is then thoroughly rinsed in the reagent (2), and

3) Subsequently the tissue section is covered with 430 $\mu$l of the reagent (3). To this is added 1.25 units of Taq DNA polymerase and the whole is heated for five minutes at 95° C. followed by thirty heat cycles of two minutes at 58° C., 1.5 minutes at 75° C. and 1 minute at 95° C. The action is finished by heating for ten minutes at 72° C.

4) The slide is then rinsed thoroughly in reagent (2) and viewed under an epifluoresence microscope.

Reagents for Kit 1 in situ measles detection

Reagent 1 (RT buffer—inc.primers)

q
10×PCR buffer
$MgCL_2$
dNTPs
RNA Guard
Random Hexamers
DEPC treated water
At required final
working concentration
Reagent 2 (Washing buffer)
phosphate buffered saline Ph 7.5
Reagent 3 (PCR buffer—inc.primers)
10×PCR buffer
$MGCL_2$
DNTPS
Primer 1) either 5' modified
Primer 2) or +Dig-UTP
Sterile double distilled water
At required final
working concentration
Enzymes
M-MLV RT—(Eg Gibco BRL)
Taq DNA polymerase—(eg Gibco BRL)

EXAMPLE 8 b) Measles nucleic acid detection bv amplification in vitro Kit 2

It is assumed that total RNA will have been prepared from tissues of interest for example by the method of Chirgwin et al (1979) Biochemistry, 18, 5294–5299, the diagnostic test may then be effected by the following steps:

1) To 0.4 $\mu$g of RNA add sufficient 5×reagent (4) 1 and DEPC treated sterile double distilled water to make up volume to 20 $\mu$l.

2) Remove an aliquot (containing 100 ng) of total RNA for an internal control reverse transcriptive PCR using the low copy number cellular UIA RNA as a target for amplification;

3) Perform hybrid capture on UIA positive RNA samples using magnetic beads with amino-linked oligonucleotide specific for both positive and negative measles RNA strands;

4) Separate the magnetic beads and elute measles RNA with 50 µl of elution buffer;

5) Use 5 µl of eluent for measles reverse transcription PCR together with relevant positive and negative controls.

6) Add 200 units of M-MLV RT and incubate at 42° C. for 2 hours for 30 minutes

7) Take the resultant cDNA product and purify using an Amicon Microcon 30 cartridge according to the manufacturers instructions.

8) Take 10 μl of purified cDNA product from step 3 and make up to 39 μl with a total of 10×reagent (5) and sterile double distilled water.

9) Add 1 unit of Taq DNA polymerase and heat for 10 minutes at 95° C. followed by 35 heat cycles of 58° C. for one minute, 72° C. for 1 minute and 95° C. for 1 minute. Finished with one heat cycle of 72° C. for 5 minutes 10) Take 1 μl of the reaction product from step 5 and make up to 23 μl with 10×reagent (6) and sterile double distilled water.

11) Add 1 unit of Taq DNA polymerase and heat cycle as for step 5 but for 25 rather than 35 cycles.

12) Take 18 μl of product from step 7 add 2 μl of loading dye and electrophrese on a 1% agarose gel to identify product of a desired kbp.

Reaqents for Kit 2 in vitro measles detection

| Reagents 4 (RT buffer) | Reagent 5 (PCR buffer 1) - inc primers | Reagent 6 (PCR buffer 2) - inc primers |
|---|---|---|
| RT buffer | PCR buffer | PCR buffer |
| DTT | $MgCL_2$ | $MgCL_2$ |
| dNTPs | W - 1 | W - 1 |
| RNase inhibitor | dNTPs | dNTPs |
| Oligo $(dT)_{12-18}$ | MV1) | |
| | outer primers | inner primers |
| | MV2) | MV4) |
| At 5 × working concentration | At 10 × working concentration | At 10 × working concentration |

Enzymes

M-MLV RT—(eg Gibco BRL)

Taq DNA polymerase—(eg Gibco BRL)

Additionally

DEPC treated sterile double distilled water

Amicon Microcon 30 size exclusion cartridge.

EXAMPLE 9

NASBA Amplification of Measles Virus N Gene Sequence

1. Warm NASBA buffer and primer, mix at room temperature and make up master mix for 20 μl reactions in clean room.
2. Aliquot master mix into Eppendorf tubes and add 100 ng of template RNA per reaction prepared by the method of Cosby et al 1989.
3. Maintain tubes at 65° C. for 5 minutes to denature RNA then hold at 41° C. for 5 minutes.
4. Warm enzyme mix to room temperature then add to reaction mix,
5. Incubate at 41° C. for 90 minutes in a water bath.
6. Detect reaction products via Northern blotting or use an enzyme-linked gel assay (e.g ELGA, Organon or Technika).

NASBA BUFFER

| REAGENT | VOLUME (μl) | FINAL CONCENTRATION |
|---|---|---|
| 1M Tris pH 8.5 | 200 | 40 mM |
| 1M $MgCl_2$ | 60 | 12 mM |
| 4M KCl | 87.5 | 70 mM |
| 1M DTT | 25 | 5 mM |
| 20 mM each dNTP | 50 each | 1 mM each |
| 20 mM ATP, UTP, CTP | 100 each | 2 mM each |
| 20 mM GTP | 75 | 1.5 mM |
| 100 mM ITP | 25 | 0.5 mM |
| $H_2O$ 27.5 | | |
| 1000 | μl | |

Aliquot and stored at −20° C.

PRIMER MIX

| REAGENT | VOLUME (μl) | FINAL CONCENTRATION |
|---|---|---|
| 100% DMSO | 750 | 75% |
| 50 uM Primer 1 | 20 | 1 uM |
| 50 uM Primer 2 | 20 | 1 uM |
| $H_2O$ | 1000 μl | |

Aliquot and store at −20° C.

ENZYME MIX

| REAGENT | VOLUME (μl) | FINAL CONCENTRATION |
|---|---|---|
| $H_2O$ | 969 | 1.5 M |
| 4.5 M Sorbitol | 668 | 105 ng/μl |
| 20 mg/ml BSA | 42 | 105 ng/μl |
| 0.87 U/μl Rnase 11 | 36 | 0.004 U/μl |
| 70 U/μl T7 RNA Pol. | 184 | 1.6 U/μl |
| 25.3 U/μl AMV RT | 101 | 0.32 U/μl |
| | 2000 μl | |

Aliquot and store at −70° C.

NB. Do not vortex the enzyme mix.

EXAMPLE 10

Measles RNA extraction and detection using NASBA was effected using the following steps:

1. Homogenise up to 500 mg of tissue in 3 ml total RNA isolation reagent (Advanced Biotechnologies). Total RNA extraction method is based on the single-step method of RNA isolation by Chomczynski et al. If using cells, resuspend pellet in 1 ml of reagent. If using blood, mix with 5×vol. of reagent.
2. Extract total RNA and resuspend pellet in 100 μl of DEPC treated $dH_2O$.
3. Measure optical density of extracted RNA solution and determine the RNA integrity via gel electrophoresis on a 1.5% agarose gel.
4. Remove an aliquot (containing 100 ng) of total RNA for an internal control NASBA using the low copy number cellular U1A RNA as a target for amplification.

5. Perform hybrid capture on UIA positive RNA samples using magnetic beads coated with amino-linked oligonucleotides specific for both positive and negative measles RNA strands.
6. Separate the magnetic beads and elute measles RNA with 50 µl of elution buffer.
7. Use 5 µl of eluent for measles NASBA together with relevant positive and negative controls.

Detect specific NASBA products using Enzyme Linked Gel Electrophoresis with an internal horseradish peroxidase-labelled oligonucleotide.

Measles NASBA

Measles NASBA should be performed using primers specific to the nucleoprotein region of the measles virus genome for example, primers AB20 and AB22.

Specific NASBA products should be detected using an internal oligo probe for example AB20.

| OLIGO | POSITION | SEQUENCE |
|---|---|---|
| AB20 (NASBA) (Upstream) | 1200–1219 | AGG GCA AGA GAT GGT AAG GA |
| AB22 (NASBA) (Downstream) | 1358–1379 | AAT TCT AAT ACG ACT CAC TAT AGG GGA TCA CCG TGT AGA AAT GAC A |
| AB10 (PROBE) | 1288–1308 | GTT TCA GAG ATT GCA ATG CA |

EXAMPLE 11

In situ Hybridisation Detection of Measles Virus

It is possible to detect measles virus RNA in situ in tissue sections which have been , for example, paraffin or araldite embedded or frozen, via in situ hybridisation.

Detection of hybrids can be either direct i.e. by fluorescence or autoradiography or indirect i.e. by subsequent reaction of the hybrid with a reporter molecule to allow its detection, for example, by chemiluminescence or fluorescence.

The following example method is for the identification of measles virus RNA in tissue sections employing a biotinylated single stranded RNA probe and the subsequent immuno-detection of hybrids. This probe is devised from the N gene sequence (Cosby et al 1989) and is 186 bp in length. It is specific for all nucleocapsid sequences of measles virus contained in the GenBank sequence data base but will not react with the closely related morbillivirus—canine distemper virus.

HYBRIDISATION

1. Take either semi-thin or ultra-thin sections and, if paraffin embedded, dewax and rehydrate (on slide), add 200 µl of proteinase K (1 mg ml$^{-1}$), and incubate for 15 ml at 37° C.
2. Wash in DEPC treated water and paraformaldehyde fix for 5 min.
3. Wash sections in DEPC treated water.
4. Add hybridisation buffer and incubate at 42° C. for 16 hours.
5. Wash sections in 0.6% NaCl, 10 mM HCl pH 7.0, 1mmol EDTA for 5 minutes at 25° C.
6. Rinse sections in DEPC treated water.
7. Wash sections in 45% v/v formamide in washing buffer for 30 minutes at 28° C.
8. Rinse sections in DEPC treated water.
9. Wash sections in 0.1×SSC for 60 minutes at 40° C.
10. Wash sections in 1ommol phosphate buffered saline twice for 5 minutes each at 25° C.

Solution

Hybridisation buffer (Final Concentration)
Formamide (50% v/v)
b 5×SSC
5×Denhardts solution
0.25 mg ml$^{-1}$ Salmon Sperm DNA
0.5 mg ml$^{-1}$ yeast tRNA
10% Dextran sulphate
DEPC treated water
Probe RNA≦100 nmol DETECTION (adapted from Cosby et al 1989 and McQuaid et al 1990)

1. Monoclonal mouse anti-biotin antibody at 1:40 dilution is applied at 37° C. for 30 minutes to the section.
2. Wash sections twice in excess phosphate buffered saline.
3. Add biotinylated anti-mouse antibody at a 1:90 dilution and incubate for 30 minutes (ibid) at 37° C.
4. Wash sections twice in excess phosphate buffered saline.
5. Add a 1:500 dilution of peroxidase conjugate and incubate for 30 min at 25° C.
6. Rinse the sections in excess phosphate buffered saline for 8 minutes
7. Add substrate 3-amino-9-diethylcarbazole and leave at 25° C. for 10 minutes.
8. Wash sections in running water for 10 minutes.
9. Allow to dry and view under microscope.
10. Sections can be counter stained with Mayers haematoxylin if appropriate.

A DETECTION KIT using the above technique comprises:

(a) the riboprobe;
(b) hybridisation buffer;
(c) proteinase K;
(d) Rnase A; and
(e) antibodies and detection reagents.

A positive and negative control are included where the negative control may be generated by the pre-treatment of an arbitrary, duplicated sample, with RNase A for 1 hour at 37° C. prior to hybridisation and detection. A positive control for the kit may be a sample of plasmid borne transcription template and for section detection the control could be a sample of a known SSPE infected tissue.

The kits in accordance with the present invention locate measles RNA which is indicative of Crohn's Disease from tissue samples from biopsies of the bowel and from body fluids such as blood and lymph and from faecal extracts.

The invention relates therefore to a diagnostic system for the detection of Crohn's Disease and ulcerative colitis to assay kits for utilisation of said system, and to therapeutic systems derived therefrom.

What is claimed is:

1. A diagnostic method for the detection of Crohn's Disease and/or ulcerative colitis which comprises detecting measles virus RNA in granulomas and/or lymphoid follicles in bowel tissue.

2. The diagnostic method according to claim 1 wherein virus RNA is detected by performing a nucleic acid based test in vitro.

3. The diagnostic method according to claim 2 wherein the test comprises a nucleotide amplification or hybridization reaction selected from a polymerase chain reaction (RT-PCR) or a nucleic acid based amplification reaction (NASBA).

4. The diagnostic method according to claim 3 wherein the test comprises the steps of:

(a) extracting measles RNA and detecting the same using NASBA or RT-PCR;

(b) enriching specific measles virus RNA/mRNA; and (c) repeating NASBA and RT-PCR.

5. The diagnostic method according to claim 2 wherein a buffered primer comprising a 51' modified oligonucleotide sequence specific for the reverse transcribed DNA from an RNA measles virus is used to detect the virus RNA.

6. The diagnostic method according to claim 3 wherein the test comprises a RNA template specific for a RNA measles virus.

7. The diagnostic method according to claim 2 wherein a primer or probe is attached to a reporter molecule which enables post amplification detection of the virus RNA.

8. The diagnostic method according to claim 7 wherein the reporter molecule is flurochromatic.

9. The diagnostic method according to claim 5 further comprising use of the following reagents:

(1) M-MLV-reverse transcriptase;

(2) random hexamers and/or oligo $(dT)_{12-18}$;

(3) a reaction buffer for (1) above;

(4) a PCR reaction buffer; and (5) a 5' modified PCR primer or probe with reporter molecules.

10. The diagnostic method according to claim 9 further comprising use of a positive control comprising measles virus RNA in solution at a known concentration and a negative control or means for providing same.

11. The diagnostic method according to claim 1 wherein the measles virus RNA is detected via a distinctive metabolic product selected from a gene sequence or a metabolic product thereof to form a nucleocapsid protein, a phosphoprotein, a matrix protein, a RNA polymerase complex, a hemagglutinin protein, a fusion protein and/or another characteristic product thereof detectable by an immunological method.

12. The diagnostic method according to claim 11 wherein the distinctive metabolic product is obtained from a sample of bowel tissue containing granulomas or lymphoid follicles.

13. A method for the analysis of Crohn's Disease and/or ulcerative colitis which method comprises the steps of:

(a) obtaining a sample of bowel tissue containing granulomas or lymphoid follicles from a patient, and securing the same in an enclosed reaction container;

(b) adding a reagent comprising a PCR buffer, $MgCl_2$ and DNTP random hexamers diluted aqueously to a desired dilution factor;

(c) subsequently closing the enclosed reaction container, adding M-MLV-RT and subjecting to heat cycling for at least one cycle;

(d) treating with a washing buffer;

(e) adding a buffered Taq DNA polymerase, $MgCl_2$, DNTP and a base primer or probe at a predetermined dilution and then heat cycling for at least 25 cycles to produce a labeled product;

(f) subsequently repeating step (d) and viewing for the labeled product to indicate the presence of measles virus RNA; and (g) determining whether the patient suffers from Crohn's Disease or ulcerative colitis based upon the presence or absence of the measles virus RNA.

14. A method according to claim 13 wherein the base primer or probe is a Dig-11 or fluorescent labeled base primer or probe.

15. A method for the in vitro analysis of a sample of bowel tissue containing granulomas or lymphoid follicles from a patient with Crohn's Disease and/or ulcerative colitis which method comprises abstracting measles virus RNA from bowel tissue containing granulomas or lymphoid follicles and:

(a) adding thereto a buffer further comprising DTT, DNTPs and RNase inhibitor and oligo (Dt) 12–18;

(b) adding thereto M-MLV-RT and subjecting to incubation to provide a cDNA product;

(c) purifying the product and adding thereto a PCR buffer along with $MgCl_2$, dNTPs and an outer primer or probe;

(d) subsequently adding Taq DNA polymerase and heating for at least 15 cycles, whereby a first reaction product is formed;

(e) recovering an aliquot of the first reaction product and adding buffered PCR with inner primers or probes and further Taq DNA polymerase and recycling for at least 15 cycles, whereby a second reaction product is formed;

(f) removing the second reaction product and adding a loading dye to form a dyed product and subjecting the dyed product to electrophoresis to identify a selected product band; and (g) sequencing the amplified products or hybridizing the amplified products with a homologous or heterologous specific probe to distinguish the measles virus to abstract the measles virus RNA from the tissue.

16. A method for the in vitro analysis of a sample of bowel tissue containing granulomas or lymphoid follicles from a patient with Crohn's Disease and/or ulcerative colitis which method comprises abstracting measles virus RNA from bowel tissue containing granulomas or lymphoid follicles and:

(a) adding thereto a room temperature buffer further comprising DNTP and room temperature primer or probe mixes to produce a master mix;

(b) aliquoting master mix into a reaction mixture comprising the template RNA to produce a resulting mixture, heating the resulting mixture for 5 minutes at 65° C., then at 41° C. for 5 minutes;

(c) subsequently adding the enzyme mix further comprising a RNA polymerase;

(d) incubating at 41° C. for 90 minutes in a water bath to produce a reaction product;

(e) detecting the reaction product by Northern blotting or an enzyme-linked gel assay; and (f) sequencing of the amplified products or hybridizing the amplified products with a homologous or heterologous specific probe to distinguish the measles virus.

17. A diagnostic method for the detection of Crohn's Disease and/or ulcerative colitis comprising detecting measles virus or viral particles in granulomas and/or lymphoid follicles in bowel tissue wherein the presence of said virus or particles is diagnostic of Crohn's Disease and/or ulcerative colitis.

* * * * *